(12) United States Patent
Merfeld et al.

(10) Patent No.: US 7,730,892 B2
(45) Date of Patent: Jun. 8, 2010

(54) MECHANICAL VESTIBULAR STIMULATOR

(75) Inventors: Daniel M. Merfeld, Lincoln, MA (US);
Wangsong Gong, Watertown, MA (US);
Steven D. Rauch, Watertown, MA (US);
Richard Terry, Arlington, MA (US);
Conrad Wall, III, Boston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 290 days.

(21) Appl. No.: 11/193,034

(22) Filed: Jul. 29, 2005

(65) Prior Publication Data

US 2007/0027405 A1    Feb. 1, 2007

(51) Int. Cl.
*A61B 19/00* (2006.01)

(52) U.S. Cl. .................................... 128/897

(58) Field of Classification Search ............... 128/897; 600/26–27; 607/42, 55–57, 62
See application file for complete search history.

(56) References Cited

U.S. PATENT DOCUMENTS

| | | | |
|---|---|---|---|
| 4,558,703 A | 12/1985 | Mark | |
| 4,592,359 A | 6/1986 | Galbraith | |
| 4,754,748 A | 7/1988 | Antowski | |
| 4,984,579 A | 1/1991 | Burgert et al. | |
| 5,658,322 A | 8/1997 | Fleming | |
| 5,919,149 A | 7/1999 | Allum | |
| 5,922,016 A | 7/1999 | Wagner | |
| 5,951,596 A | 9/1999 | Bellinger | |
| 5,984,859 A | 11/1999 | Lesinski | |
| 6,063,046 A | 5/2000 | Allum | |
| 6,078,838 A | 6/2000 | Rubinstein | |
| 6,176,837 B1 | 1/2001 | Foxlin | |
| 6,217,525 B1 | 4/2001 | Medema et al. | |
| 6,219,578 B1 | 4/2001 | Collins et al. | |
| 6,219,580 B1 | 4/2001 | Faltys et al. | |
| 6,295,472 B1 | 9/2001 | Rubinstein et al. | |
| 6,314,324 B1 | 11/2001 | Lattner et al. | |
| 6,358,272 B1 | 3/2002 | Wilden | |
| 6,409,687 B1 | 6/2002 | Foxlin | |
| 6,430,443 B1 | 8/2002 | Karrell | |
| 6,546,291 B2 | 4/2003 | Merfeld et al. | |
| 6,735,475 B1 | 5/2004 | Whitehurst et al. | |

(Continued)

FOREIGN PATENT DOCUMENTS

WO    WO2004/045242    5/2004

(Continued)

OTHER PUBLICATIONS

Wells et al. "Optical stimulation of neural tissue in vivo". Optics Letters 30(5):504-506, Mar. 1, 2005.

(Continued)

*Primary Examiner*—Charles A Marmor, II
*Assistant Examiner*—Christine D Hopkins
(74) *Attorney, Agent, or Firm*—Occhiuti Rohlicek & Tsao LLP

(57) ABSTRACT

An apparatus to stimulate the vestibular system of an individual. The apparatus comprises an actuator configured to mechanically stimulate a semicircular canal, and a control module coupled to the actuator that controls the actuator in response to motion information associated with the individual.

18 Claims, 5 Drawing Sheets

U.S. PATENT DOCUMENTS

| | | | |
|---|---|---|---|
| 6,748,275 B2 * | 6/2004 | Lattner et al. | 607/42 |
| 6,830,580 B2 | 12/2004 | Neuberger | |
| 6,921,413 B2 | 7/2005 | Mahadevan-Jansen et al. | |
| 7,225,028 B2 | 5/2007 | Della Santina et al. | |
| 7,488,341 B2 | 2/2009 | Merfeld | |
| 2002/0072781 A1 | 6/2002 | Lattner et al. | |
| 2003/0171787 A1 | 9/2003 | Money et al. | |
| 2003/0195588 A1 | 10/2003 | Fischell et al. | |
| 2004/0006287 A1 | 1/2004 | Epley | |
| 2004/0167415 A1 | 8/2004 | Gelfand et al. | |
| 2004/0199223 A1 | 10/2004 | Andersen et al. | |
| 2004/0215236 A1 | 10/2004 | Lattner et al. | |
| 2005/0201574 A1 * | 9/2005 | Lenhardt | 381/151 |
| 2005/0216072 A1 | 9/2005 | Mahadevan-Jansen et al. | |
| 2005/0222644 A1 | 10/2005 | Killian et al. | |
| 2005/0267549 A1 | 12/2005 | Della Santina et al. | |
| 2006/0004422 A1 | 1/2006 | De Ridder | |
| 2006/0079950 A1 | 4/2006 | Lehnhardt et al. | |
| 2006/0161227 A1 | 7/2006 | Walsh et al. | |
| 2006/0161255 A1 * | 7/2006 | Zarowski et al. | 623/10 |
| 2007/0012321 A1 | 1/2007 | Zelinsky | |
| 2007/0027405 A1 | 2/2007 | Merfeld et al. | |
| 2007/0027465 A1 | 2/2007 | Merfeld et al. | |
| 2007/0038268 A1 | 2/2007 | Weinberg et al. | |
| 2007/0100263 A1 | 5/2007 | Merfeld | |
| 2007/0167985 A1 | 7/2007 | Kirby | |
| 2008/0172102 A1 | 7/2008 | Shalev | |

FOREIGN PATENT DOCUMENTS

| | | |
|---|---|---|
| WO | WO2004/060015 | 7/2004 |
| WO | WO2007/015778 | 2/2007 |
| WO | WO2007/016061 | 2/2007 |
| WO | WO2007/030337 | 3/2007 |
| WO | WO2007/033290 | 3/2007 |

OTHER PUBLICATIONS

Gong et al. "Prototype Neural Semicircular Canal Prosthesis Using Patterned Electrical Stimulation". Annals of Biomedical Engineering, vol. 28, pp. 572-581, 2000.

Wall et al. "Vestibular Function and Anatomy". Department of Otolaryngology—Head and Neck Surgery, University of Texas Medical Branch, Galveston, TX, pp. 1891-1901.

"System Design and Performance of a Unilateral Horizontal Semicircular Canal Prosthesis" by Gong et al., IEEE Transactions on Biomedical Engineering, vol. 49, No. 2, Feb. 2002, pp. 175-181.

Merfeld et al. "Ch. 7.7—*Vestibular Prosthetics*". Neuroprosthetics: Theory and Practice, K. Horch and G. Dhillon, Editors. 2002.

Wall et al. "Vestibular Prostheses: the Engineering & Biomedical Issues". Journal of Vestibular Research 11:1-19, 2002.

International Preliminary Report on Patentability for Application No. PCT/US2006/027535 dated Feb. 7, 2008.

U.S. Appl. No. 11/195,568, Merfeld et al., filed Aug. 1, 2005.

U.S. Appl. No. 11/227,969, Merfeld et al., filed Sep. 14, 2005.

U.S. Appl. No. 11/261,394, Merfeld et al., filed Oct. 27, 2005.

Rabbitt et al., "The influence of surgical plugging on horizontal semicircular canal mechanics and afferent response dynamics", J. Neurophysiology, vol. 82, pp. 1033-1052 (1999).

International Preliminary Report on Patentability in Application No. PCT/US2006/028756, dated Mar. 10, 2009 (includes Int'l Search Report & Written Opinion dated Jun. 30, 2008).

International Preliminary Report on Patentability in Application No. PCT/US2006/027535, dated Jan. 29, 2008, (includes Int'l Search Report & Written Opinion dated Jul. 25, 2007).

International Preliminary Report on Patentability in Application No. PCT/US2006/35759 dated Mar. 18, 2008, (includes Int'l Search Report & Written Opinion dated Jul. 26, 2007).

International Preliminary Report on Patentability in Application No. PCT/US2006/033126, dated Mar. 10, 2009, (includes Int'l Search Report & Written Opinion dated Jun. 25, 2008).

Action and Response History in U.S. Appl. No. 10/738,920, retrieved from PAIR on Jul. 22, 2009.

Action and Response History in U.S. Appl. No. 11/351,388, retrieved from PAIR on Jul. 22, 2009.

Action and Response History in U.S. Appl. No. 11/195,568, retrieved from PAIR on Jul. 22, 2009.

Action and Response History in U.S. Appl. No. 11/261,394, retrieved from PAIR on Jul. 22, 2009.

Action and Response History in U.S. Appl. No. 11/227,969, retrieved from PAIR on Jul. 22, 2009.

* cited by examiner

MECHANICAL VESTIBULAR STIMULATOR

TECHNICAL FIELD

This invention relates to a medical prosthesis, and more particularly to a vestibular prosthesis.

BACKGROUND

The ability of human beings to maintain stability and balance is controlled by the vestibular system. This system provides the central nervous system with the information needed to maintain balance and stability.

FIG. 1 is a diagram showing the vestibular system. As shown, the vestibular system includes a set of ring-shaped tubes, referred to as the semicircular canals 102a-c, that are filled with the endolymph fluid. The semicircular canals are formed by a membrane called the membranous labyrinth. Each of the semicircular canals 102a-c is disposed inside a hollow bony tube (not shown in the diagram) called the bony labyrinth that extends along the contours of the semicircular canals. Lining the interior walls of the bony labyrinth is a thin membrane called the endosteum. The bony labyrinth is filled with a fluid called the perilymph. As further shown in FIG. 1, each semicircular canal 102a-c terminates in an enlarged balloon-shaped section called the ampulla (marked 104a-c in FIG. 1). Inside each ampulla is the cupula 106a-c, on which hair cells are embedded. Generally, as the semicircular canals 102a-c rotate due to rotational motion of a head, the endolymph fluid inside the canal will lag behind the moving canals, and thus cause the hair cells on the cupula to bend and deform. The deformed hair cells stimulate nerves attached to the hair cells, resulting in the generation of nerve signals that are sent to the central nervous system. These signals are decoded to provide the central nervous system with motion information. The three canals are mutually orthogonal and together provide information about rotation in all three spatial dimensions. The other endorgans in the vestibular system are the otolith organs, the utricle and the saccule. These endorgans act as linear accelerometers and respond to both linear motion and gravity.

In response to the vestibular nerve impulses, the central nervous system experiences motion perception and controls the movement of various muscles thereby enabling the body to maintain its balance.

When some hair cells of peripheral vestibular system are damaged, but others remain viable (as often happens in situations involving bilateral vestibular hypofunction), a person's ability to maintain stability and balance will be compromised. Persons with improperly functioning vestibular systems may consequently experience vertigo, dizziness, and clumsiness, which may lead to collisions and spontaneous falls.

To remedy damaged peripheral vestibular systems, prostheses based on electrical stimulation are being developed. Such prostheses use implanted or non-implanted transmitting electrodes to cause electric stimulation of a target nerve (e.g., vestibular nerve ganglion cells). Such electric stimulation results, for example, in corresponding reflexive responses in the vestibulo-ocular and the vestibulo-spinal pathways, thereby enabling the person to maintain balance and stability in response to the electrical stimulation. Alternatively, such electrodes can target nerves not located in the vestibular system. Electrical stimulation does not involve the actuation of the peripheral vestibular system's hair cells, and thus this type of stimulation lacks a natural feel and makes a person's adaptation to this type of stimulation more difficult.

SUMMARY

In one aspect, the invention includes apparatus to stimulate the vestibular system of an individual. The apparatus comprises an actuator configured to mechanically stimulate a semicircular canal, and a control module coupled to the actuator that controls the actuator in response to motion information associated with the individual.

In some embodiments, the apparatus further comprises a sensing system that provides motion information to the actuator.

In certain embodiments, the control module of the apparatus is configured to control the actuator by generating a control signal for transmission to the actuator. In some embodiments the control signal includes data to control at least one of an adjustable frequency, an adjustable amplitude, and an adjustable duration of actuation.

In some embodiments, the actuator comprises a balloon attached to a catheter, the balloon having a volume that varies in response to a control signal. In some embodiments the actuator comprises a piezoelectric mechanical vibrator, the vibrator being configured to be displaced in response to a control signal. In some embodiments the actuator comprises a piston, the piston being configured to be displaced in response to a control signal. In some embodiments the actuator comprises an elastic membrane, the elastic membrane being configured to expand in response to a control signal.

In some embodiments the apparatus further comprises a power source electrically coupled to the actuator to power the actuator.

In another aspect, the invention includes a method for stimulating the vestibular system. The method comprises inserting an actuator in mechanical communication with a semicircular canal of a patient, detecting a signal indicative of motion of the patient, and causing the actuator to displace the semicircular canal in response to the signal.

In another aspect, the invention includes an apparatus for stimulating the vestibular system of a subject. The apparatus comprises one or more actuators placed in mechanical communication with corresponding semicircular canals, and a control module configured for controlling the mechanical actuation of the one or more actuators in response to motion information associated with the subject.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference symbols in the various drawings indicate like elements.

DETAILED DESCRIPTION

Figure 1:
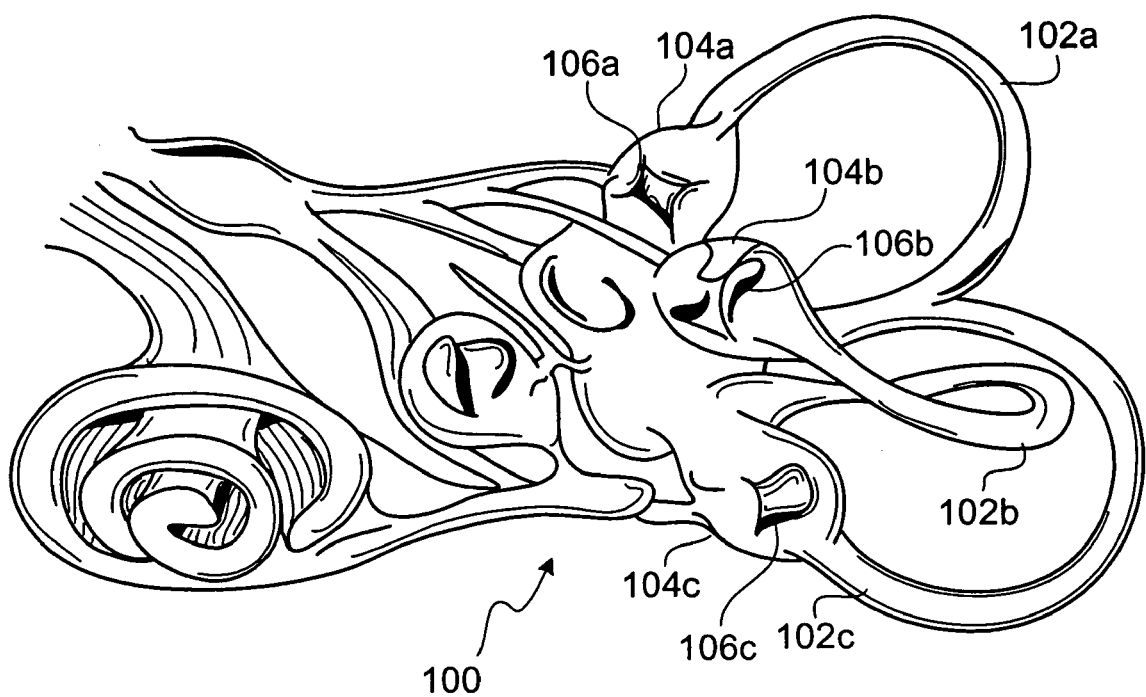
FIG. 1 is a diagram of part of the vestibular system.
Figure 2:
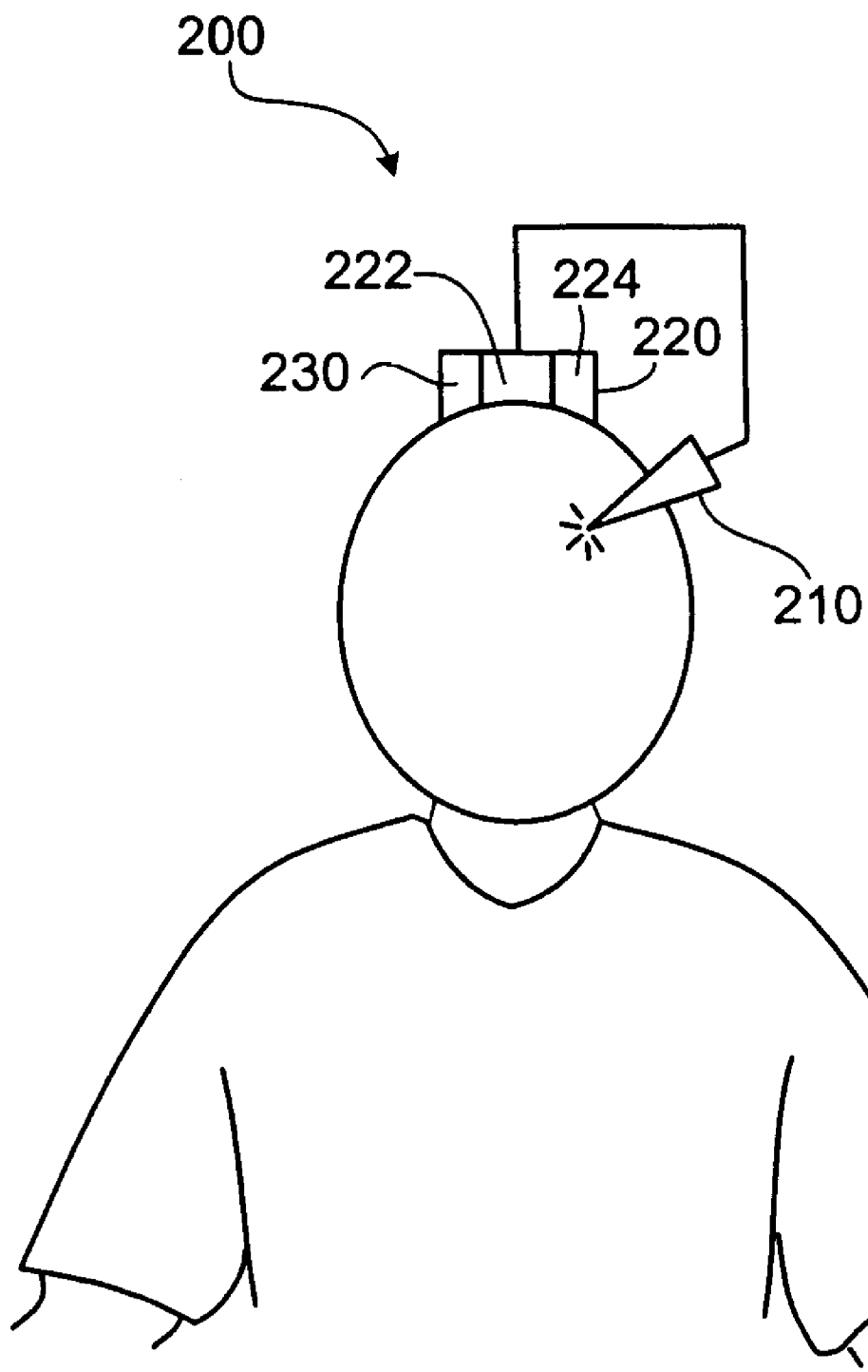
FIG. 2 is a schematic diagram of an embodiment of a mechanical vestibular stimulator.
Figure 3A:
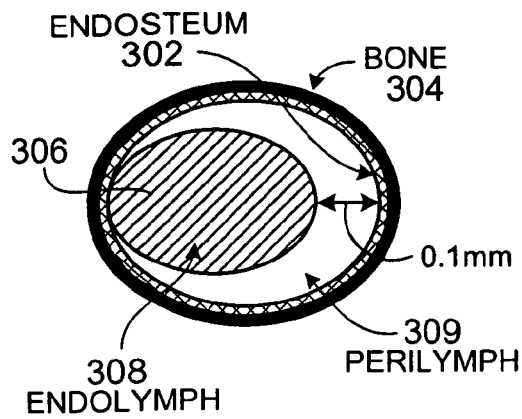
FIG. 3A is a schematic diagram in cross-section of a semicircular canal in the vestibular system.

FIG. 2 is a schematic diagram of a vestibular stimulator apparatus 200 to stimulate the vestibular system of a person chronically for days, weeks, months, or longer, at a time. As can be seen, the stimulator 200 includes an actuator 210 inserted proximate to a semicircular canal to be actuated. FIG. 3A is a simplified cross-sectional diagram of the semicircular canal that is to be actuated to stimulate the vestibular system. As shown, the semicircular canal 306 is formed from the membranous labyrinth. Endolymph fluid 308 fills the canal 306. A bony labyrinth 304 lined with endosteum 302 defines a volume filled with perilymph fluid 309 that surrounds the canal 306. Actuation of the actuator 210 displaces the semicircular canal inside the perilymph-filled volume formed by the bony labyrinth, thereby causing motion of the endolymph. The moving endolymph causes the hairs on the cupula to move or bend in response to the extent of the actuation. The actuator thus, in effect, amplifies the movement of the endolymph, thereby causing the hairs to bend more than they would otherwise. This provides additional stimulation to the nerves associated with these hairs. By effectively amplifying the input signal in this way, the actuator functions in a manner analogous to a hearing aid.

The actuator 210 include a control mechanism (not shown) that receives control signals transmitted from the control module 220. Transmission of control signals from the control module 220 to actuator 210 can be done using wireless transmission. Alternatively, the control signals can be sent from an electrical wire connecting the control module 220 to the actuator 210. The wire is placed inside a catheter that runs subcutaneously from the control module 220 to the control mechanism of the actuator 210.

FIGS. 3B-3E are various embodiments of the actuator 210. In the embodiment shown in cross-section in FIG. 3B, an actuator 310 includes a piston 312 that is displaced hydraulically inside a cylinder 316. The dimensions of the mechanical piston depend on the size of the semicircular canal, which in turn depends on the patient's age and gender. A typical piston diameter for an adult male is 0.3-1.0 mm. Control signals received by the piston's control mechanism (not shown) from the control module 220 (shown in FIG. 2) determine the extent, the frequency, and/or duration with respect to which the piston 312 is to be displaced.

Displacement of the piston depends on the linear and rotational displacement of the person's head. Thus, for example, if a person's head experiences a particular angular acceleration over a particular time, the extent of the piston's actuation, both in terms of its displacement of the piston 312 in the cylinder 316 and the frequency at which the piston slides back and forth in the cylinder will be commensurate with the acceleration of the head.

As the piston is displaced, it presses against the endosteum 302. This causes the endosteum 302 to be displaced inwardly. The displacement of the endosteum 302 displaces the semicircular canal cupula, thereby causing the hair cells in the cupula to be deflected.

To minimize damage to the endosteum 302 due to the piston's motion, the piston head is covered with a soft biocompatible material 314. A suitable biocompatible material is Silastic.

Since the actuator 310 is implanted, it should be constructed using biocompatible materials. Thus, in some embodiments the piston-based actuator 310 is made of suitable metallic materials such as stainless steel or titanium. Other suitable materials include various types of ceramics that are approved for medical applications.

Figure 3B:
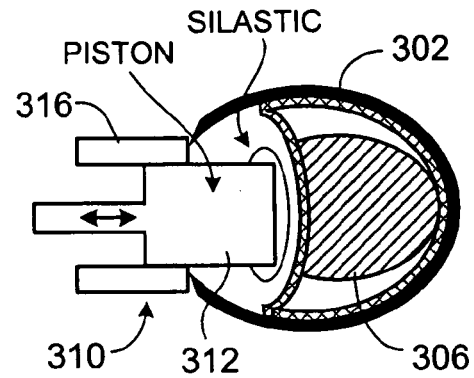
FIG. 3B is a schematic diagram in cross-section of an embodiment of a piston-based actuator.
Figure 3C:
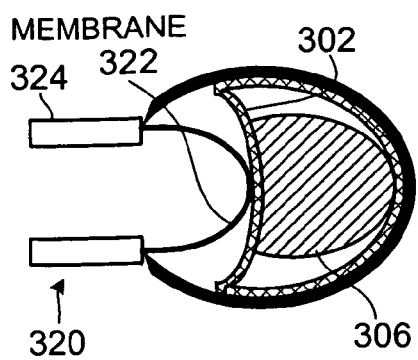
FIG. 3C is a schematic diagram in cross-section of an embodiment of an elastic membrane actuator.

FIG. 3C shows in cross-section a second embodiment of an actuator. In the embodiment shown in FIG. 3C, an actuator 320 includes an elastic membrane 322 placed at the end of a cylinder 324. Pressure provided by a pump mechanism coupled to the actuator via the cylinder 324 causes the membrane 322 to expand outwardly towards the endosteum, thereby deflecting the endosteum 302. As with the piston-based actuator shown in FIG. 3B, deflection of the endosteum 302 shifts the position of the semicircular canal cupula, causing the hair cells on the cupula to be deflected. Additionally, the actuator 320 includes a control mechanism (not shown) adapted to receive control signals from the control module 220. These control signals cause the actuator's pump to pump fluid (gas and/or liquid) to the extent required to expand the membrane 322 in response to acceleration of the person's head.

Figure 3D:
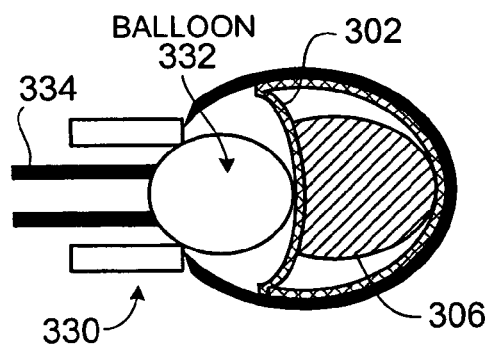
FIG. 3D is a schematic diagram in cross-section of an embodiment of a balloon actuator implanted at the exterior of the bony labyrinth.

FIG. 3D shows in cross-section a third embodiment of an actuator. In the embodiment shown in FIG. 3D, an actuator 330 includes a balloon 332 in fluid communication with a balloon catheter 334. Pressure provided by a pump mechanism (not shown) coupled to the actuator via the cylinder 324 causes the balloon 332 to expand outwardly towards the endosteum 302, thereby deflecting the endosteum 302. As with the piston-based actuator 310 shown in FIG. 3B, deflection of the endosteum 302 results in the contraction of the inner volume defined by the endosteum 302, which in turn shifts the semicircular canal, thereby causing the hair cells on the cupula to be deflected. Additionally, the actuator 330 includes a control mechanism (not shown) adapted to receive control signals from the control module 220 to cause the actuator's pump to pump fluid to the extent required to inflate the balloon 332 in response to the acceleration of the person's head.

The actuators shown in FIGS. 3B-3D are placed on the exterior of the endosteum. As a result, the endosteum 302 is not breached. This reduces the risk of damage that can otherwise be caused by the presence of an actuator in the perilymph space (i.e., in the volume defined by the bony labyrinth 304 and the endosteum 302).

Figure 3E:
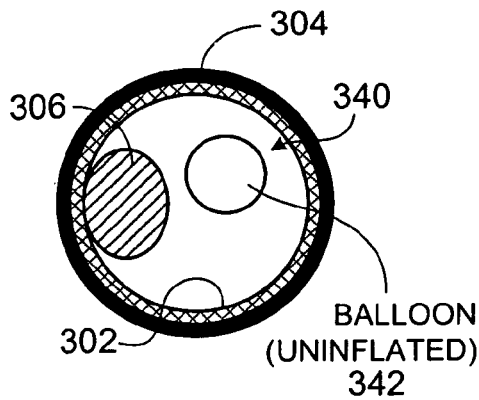
FIG. 3E is a schematic diagram in cross-section of an embodiment of a balloon actuator implanted at the interior of the bony labyrinth.
Figure 3F:
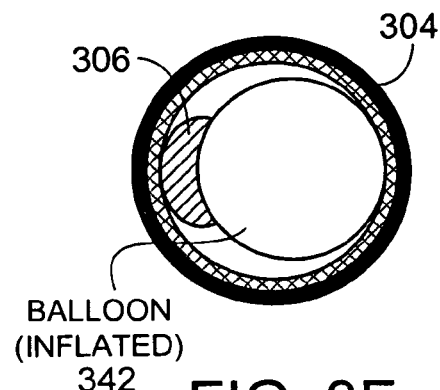
FIG. 3F is a schematic diagram in cross-section of the balloon actuator of FIG. 3E in operation.

FIGS. 3E-F show in cross-section a fourth embodiment of an actuator. In this case, the actuator is placed inside the perilymph space. As shown in FIG. 3E, an actuator 340 includes a balloon 342 coupled to a balloon catheter (not shown). The balloon 342 is constructed of a material that is durable, non-porous, has good elongation properties (e.g., greater than 250% of the original size of the balloon), and has proper tensile strength. Example of such materials include latex, polyurethane, and silicone elastomers. It should be noted that if latex is selected as the material of choice for constructing the balloon 342, then medical grade latex, in which proteins causing allergic reaction have been removed, should preferably be used. The balloon 342 generally has a length of about 1 mm, an inflated circular cross-section diameter of 0.7-1 mm, and a deflated circular cross-section diameter of approximately 0.2-0.3 mm.

The balloon catheter is inserted into the perilymph space by cutting a small opening through the bony labyrinth 304 and the endosteum 302. The balloon catheter may subsequently be inserted into the perilymph space using a micromanipulator. After insertion of the balloon catheter, the openings in the bony labyrinth and endosteum are sealed and allowed to heal.

Actuator 340 also includes a larger diameter catheter (also not shown) located outside the bony labyrinth that is coupled to the smaller catheter that was inserted into the perilymph space. The larger catheter runs subcutaneously to a closed container in which a pump mechanism, a fluid reservoir for inflating the balloon, and a control mechanism to control the actuation of the balloon 342 are all located. (The pump mechanism, fluid reservoir, and the control mechanism are of conventional design and are therefore omitted from FIGS. 3E-F for the sake of clarity).

The control mechanism for the balloon actuator shown in FIGS. 3E-F is adapted to receive control signals from the control module 220 and to cause the pump to pump fluid into the balloon 342 to the extent required to deflect the semicircular canal 306 in response to the linear or angular acceleration of the person's head.

Thus, with reference to FIG. 3F, the pump mechanism directs pressurized gas or liquid from the fluid reservoir through the interconnected catheters. This fluid inflates the balloon 342 inside the perilymphs space, thereby deflecting the cupula of the semicircular canal 306. The deflection of the semicircular canal 306 in turn causes the deflection of the hair cell on the cupula. To deflate the balloon so as to enable bidirectional actuation of the balloon and/or the semicircular canal 306, the pump mechanism withdraws the gas/liquid pumped into the balloon 342.

The fluid reservoir used to inflate the balloon should have enough fluid to ensure that the balloon-based actuator 340 would continue operating notwithstanding any fluid leakage. In some embodiments the reservoir has enough fluid to fill four (4) orders of magnitude of the volume occupied by the inflated balloon 342. The fluid reservoir is preferably equipped with a recharging mechanism so that when the fluid level in the reservoir dips below a certain threshold level, the reservoir could be recharged to ensure continued operation of the actuator 340.

It will be clear that the use of the pump mechanism together with the fluid reservoir described in relation to the actuator 340 can equally be used to actuate the balloon based actuators shown in FIGS. 3C and 3D.

Yet another embodiment of the actuator 210 shown in FIG. 2 is one that is based on a piezoelectric device. By transmitting voltage signals corresponding to the movement of a person from the control module 220 to a piezoelectric device, which is placed proximate to the endosteum, the piezoelectric device will consequently be displaced in accordance with the level of the signal it receives, and thereby actuate the endosteum 302. Actuation of the endosteum 302 would consequently cause the endosteum to retract and expand. This, in turn, causes the cupula of the semicircular canal 306 to shift, thereby causing the hair cells on the cupula to deform and send corresponding motion signals to the central nervous system. Alternatively, the piezoelectric device could be used to push fluid to activate any of the balloon-like actuators 322 332, 342 discussed previously. Alternatively, a piston could be moved by the piezoelectric device to push directly on the endosteum.

Yet another embodiment uses a magnetic field created by a coil of wire to move a piston electromagnetically, which, in turn, pushes fluid to activate any of the balloon-like actuators 322 332, 342 discussed previously. Alternatively, the piston moved by the magnetic coil could push directly on the endosteum 302.

Other types of actuators for actuating the semicircular canal and triggering motion signals to be sent to the central nervous system are also possible.

As noted above, and as can be seen from FIGS. 3B-3F, the actuator is adjacent to the endosteum 302 (either outside the endosteum, or inside the perilymph space). Placement of the actuator either outside or inside the endosteum 302 generally includes a surgical procedure to, among other things, remove part of the bony labyrinth shielding the endosteum. Thus, performance of such a surgical procedure would generally require that at least local anesthesia be used.

Turning back to FIG. 2, although only a single actuator 210 is shown, it will be readily understood that the vestibular stimulator may include additional actuators. For example, a companion actuator (not shown in the figure) may be placed in the person's other ear. Use of such an additional actuator would be particularly useful to provide symmetric stimulation to alleviate bilateral vestibular conditions that affect a person's left and right vestibular organs (i.e., both ears). Further, use of multiple actuators may also be desirable to more accurately mimic the complementary functioning of a person's bilateral (left and right side) peripheral vestibular organs. Further, it will also be understood that more than one actuator may be placed in each of a person's ears. For example, actuators may be placed in each of the three orthogonal semicircular canals forming a person's peripheral vestibular system.

As further shown in FIG. 2, coupled to actuator 210 is control module 220. control module 220 controls the mechanical actuation of the actuator 210, including the amplitude, frequency, and/or duration of the actuations caused by the actuator 210. Control signals generated by the control module 220 are transmitted to the actuator 210. As previously noted with respect to the various shown embodiments in FIGS. 3B-F of the actuator 210, the actuator 210 includes a receiver and control mechanism that receive the control signals and use the received signals to produce the actuations in accordance with the received control signals.

The control module 220 includes motion sensing system 222 that determines the person's movement including rotation, translation, and/or orientation with respect to gravity Examples of a motion sensing system are provided in U.S. Pat. No. 6,546,291, entitled "Balance Prosthesis", the contents of which are hereby incorporated by reference in its entirety. Generally, the motion sensing system includes translation sensors and rotational sensors. The translation sensors typically include three translation sensors configured to sense the person's translation along the three coordinate axes and/or three rotation sensors configured to sense rotations along the three axes.

Figure 4:
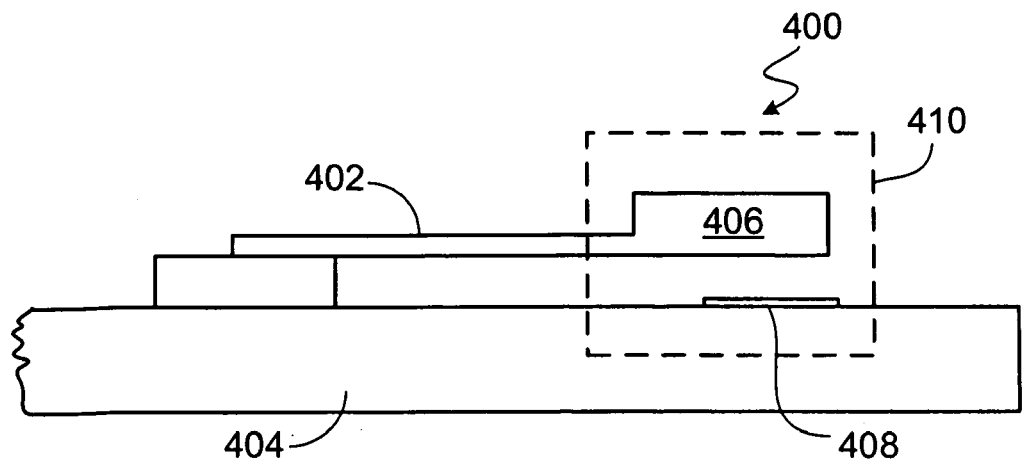
FIG. 4 is a translation sensor for use with the mechanical vestibular stimulator of FIG. 2.

An exemplary translation sensing device 400 is shown in FIG. 4. As shown, the translation sensing device 400 is a micro-mechanical device on which a cantilevered beam 402 is mounted on a substrate 404. The cantilever 402 suspends a proof mass 406 above a sense electrode 408. The proof mass 406 and the sense electrode 408 together form a capacitor 410 having a capacitance that depends in part on the gap separating the proof mass 406 from the sense electrode 408. An acceleration normal to the substrate 404 results in a force that deflects the proof mass 406 toward or away from the sense electrode 408, thereby changing the capacitance. This change in capacitance modulates a signal, which thus carries information indicative of acceleration normal to the cantilevered beam 402.

Figure 5:
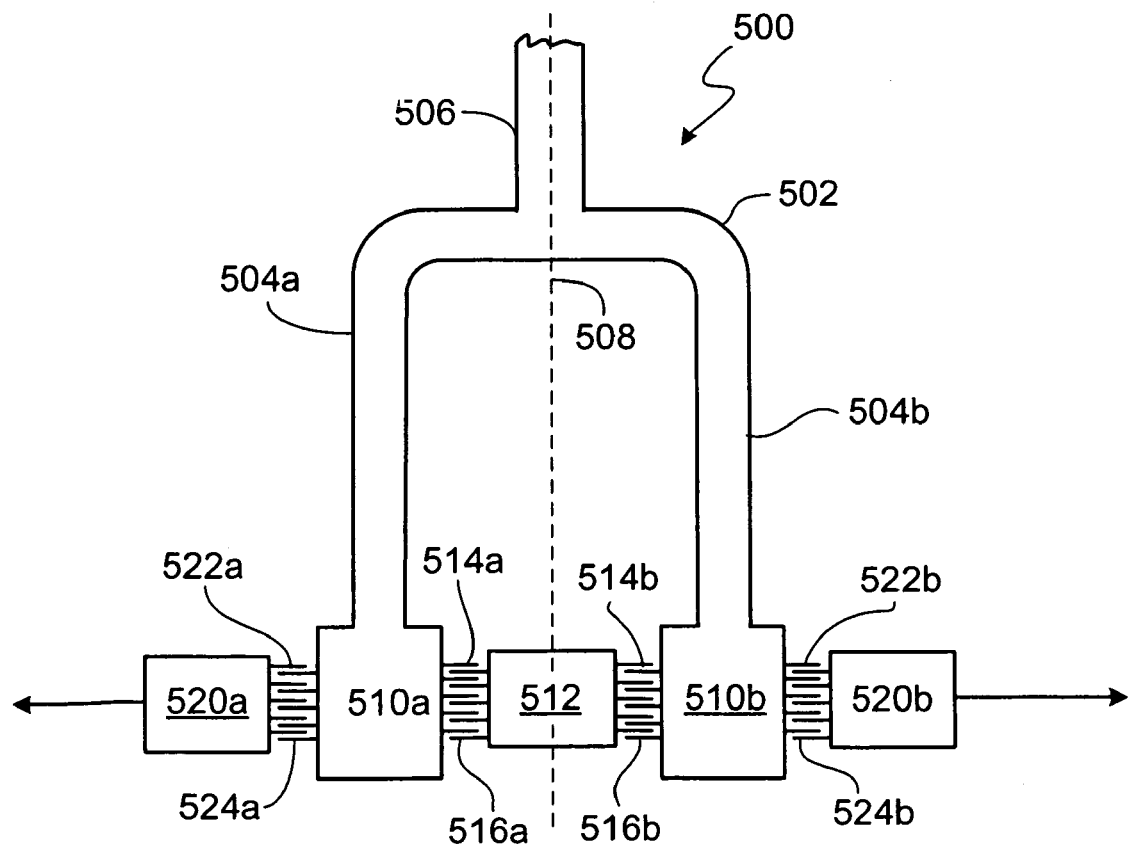
FIG. 5 is a plan view of a rotation sensor for use with the mechanical vestibular stimulator of FIG. 2.

FIG. 5 is an exemplary rotation sensing device 500. As shown, rotation sensing device 500 is a micro-mechanical device that includes a tuning fork 502 having first and second parallel tines 504a, 504b connected to a base 506. A line extending through the base 506 and parallel to the first and second tines 504a, 504b defines a central axis 508 of the tuning fork 502. The first and second tines 504a, 504b of the tuning fork 502, when the tuning fork 502 is in its equilibrium position, define an equilibrium plane. First and second proof masses 510a, 510b are integrated onto the ends of the first and second tines 504a, 504b respectively.

The rotation sensor 500 also includes an inner comb 512 disposed between the first and second proof masses 510a, 510b. The inner comb has two sets of teeth 514a, 514b, each of which extends away from the central axis 508 in the equilibrium plane. Each proof mass 510a, 510b includes a plurality of inner teeth 516a, 516b extending toward the central axis in the equilibrium plane. These inner teeth 516a, 516b interdigitate with the corresponding teeth 514a, 514b extending from the inner comb 512.

The rotation sensor 500 also includes two outer combs 520a, 520b, each disposed adjacent to a proof mass 510a, 510b. Each outer comb 520a, 520b has a plurality of teeth 522a, 522b extending inwardly toward the central axis 508 in the equilibrium plane. Each proof mass 510a, 510b includes a plurality of outer teeth 524a, 524b that extend away from the central axis 508 in the equilibrium plane. These outer teeth 524a, 524b interdigitate with the corresponding teeth 522a, 522b on the outer combs 520a, 520b.

Figure 6:
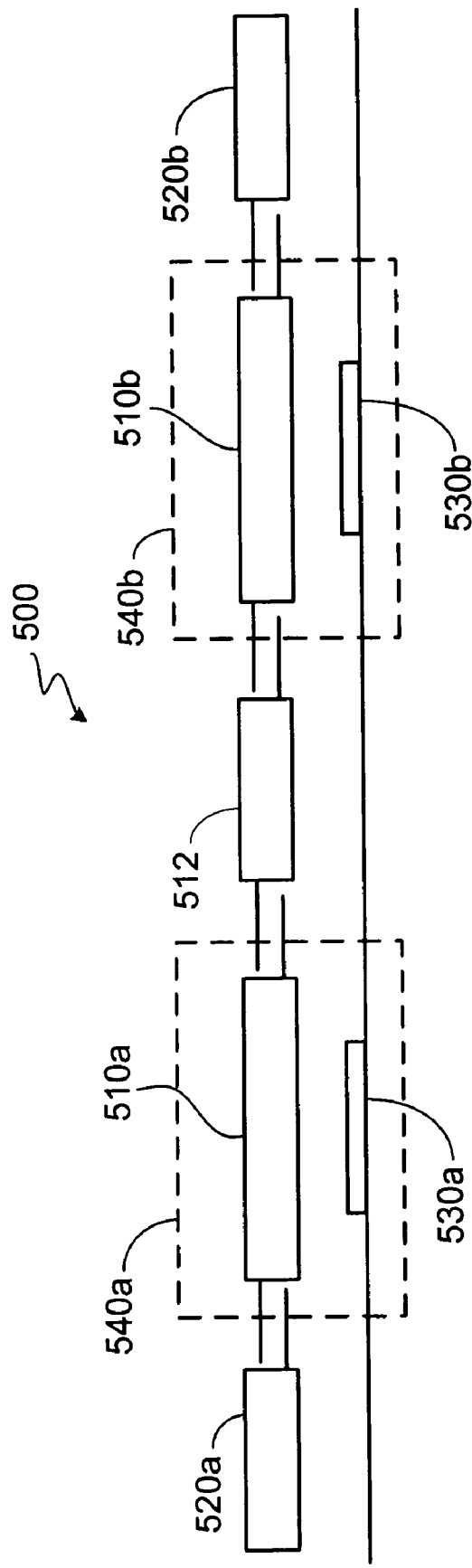
FIG. 6 is a cross-sectional view of the rotation sensor of claim 5.

The proof masses 510a, 510b are suspended above first and second sense electrodes 530a, 530b, as shown in the cross-section of FIG. 6. Each proof mass 510a, 510b and its corresponding sense electrode 530a, 530b thus defines a capacitor 540a, 540b having a capacitance that depends on the position of the proof mass 510a, 510b relative to the sense electrode 530a, 530b.

The inner and outer combs 512, 520a, 520b are connected to a voltage source that generates a voltage on their respective teeth 514a, 514b, 522a, 522b. This results in the generation of an electrostatic force that deflects the proof masses 510a, 510b in the equilibrium plane. The voltage on the teeth 514a, 514b, 522a, 522b of the inner and outer combs 512, 520a, 520b is selected to cause oscillation of the proof masses 510a, 510b in the equilibrium plane. To maintain oscillation, the rotation sensor consumes approximately 0.2 watts from a 5 volt DC source. The oscillation of the proof masses 510a, 510b results in the generation of an equilibrium angular momentum vector that is perpendicular to the equilibrium plane and an equilibrium capacitance signal measured at the sense electrodes 530a, 530b.

When the person wearing the rotation sensor 500 experiences a rotation, the angular momentum vector points in a different direction relative to a fixed reference frame associated with the wearer's surroundings. Because angular momentum of the oscillating proof masses 510a, 510b is conserved, a torque is generated that causes the proof masses 510a, 510b to oscillate above and below the equilibrium plane. This causes the angular momentum vector to recover its original direction.

As the proof masses 510a, 510b oscillate above and below the equilibrium plane, the capacitance of the capacitors 540a, 540b changes. This change provides a signal indicative of rotational motion experienced by the rotation sensor 500. The dynamic response of the rotation sensor 500 has a bandwidth between 100 and 1000 Hz and a maximum rate range of 400 degrees per second.

It will be understood that other types of translation and rotation sensors having different configurations and designs may be used instead of the translation and/or rotation sensors shown in FIG. 4 and FIGS. 5-6 respectively.

Returning to FIG. 2, the motion sensing system 222, which includes one or more sensing instruments such as a translation sensing device 400 and/or rotation sensing device 500, is secured to the person's head, thereby enabling the sensing device to sense motion of the person's head. The relatively small size of the sensing system 222 enables placement of the sensing system 222 on the external surface of the head, preferably at an inconspicuous and unobtrusive location. Alternatively, the sensing system 222 may be placed underneath the surface of the head, or at other locations on the person's body.

The control module 220 also includes a computing device 224. which can perform computations using digital and/or analog techniques. The computing device 224 is configured to receive data from the various sensing devices of the motion sensing system 222, to process the data, and to generate output control information to be sent to the actuator 210. Some operations that computing device 224 is configured to perform include filtering and scaling of the input motion data.

For example, sample streams from the rotation sensing devices employed by motion sensing system 222 may be passed through integrators to obtain angular displacements. The outputs of the integrators can then be passed through high-pass filters to remove low-frequency errors introduced by variations in the rotation sensors' bias voltages. Another processing operation that can be performed by the computing device 224 includes passing motion data from the translation sensing devices employed by motion sensing system 222 through low-pass filters to remove high-frequency components contributions from the rotation sensing devices. Suitable low-pass filters include third-order Butterworth filters having −3 dB points near, for example, 0.03 Hz. The outputs of the high-pass filters that processed the rotational motion data and the low-pass filters that processed the translation motion data can then be passed through corresponding summers to obtain an estimate of the wearer's orientation in an inertial coordinate system.

Other types of processing that the computing device 224 may be configured to perform can also include the implementation of a procedure to resolve the translation motion data into its various components to distinguish between acceleration that results in translation and acceleration caused by gravity. In particular, by using a pre-determined initial gravity vector g(0), and using the rotation data obtained from the rotation sensing devices, a rotation transformation can be performed to estimate the magnitude and direction of a gravity vector g(t) at any instant. This gravity vector can then be subtracted from the translation motion data to derive the three linear translation motion vectors at that instant due to linear acceleration corresponding to the actual translation of the wearer.

Another type of processing that may be performed by the computing device 224 includes the determination of the person's orientation in an inertial coordinate system.

For example, a Kalman filter that incorporates a model of the dynamic characteristics of the motion sensing system 222 and of the person can be used to derive such an estimate. The resulting estimates from the computing device 224 can be provided to an encoder for translation into a control signal that can be used actuate the actuator 210 and thereby stimulate the person's vestibular system.

The resultant control signal sent to the actuator 210 can be a continuously fed signal that causes the actuator 210 to frequently change the level of actuation. Thus, the control signal continuously transmits information regarding the amplitude of the actuation. Alternatively, the control signals sent to actuator 210 can be sent as short bursts every predetermined interval of time (e.g., every 10 ms). Control signals sent as short bursts can carry information regarding the level, duration and/or frequency of actuation. For example, based on signal level of the sensing device of the motion sensing system 222, the computing device 224 can determine a corresponding control feedback signal representing a discrete amplitude value, frequency value, and/or time duration sent to the actuator 210 so that the actuator 210 can produce mechanical actuations that cause the central nervous system to properly stabilize and balance the person's body and/or head.

The Computing device 224 also generates control signals for controlling minute and/or quasi-static changes to the actuations resulting from environmental changes and/or performance degradation from physical imperfections of the actuator 210. For example, in circumstances where the actuator 210 is a balloon-type actuator, similar to actuator 330 shown in FIG. 3D, room-temperature variation of 5° C. can cause a change in the barometric pressure in the room of 1%. Such a change in pressure can lead to a performance degradation of the balloon-based actuator, so that eventually the actuator fails to properly stimulate of the vestibular system. Additionally, over time the fluid used to control the volume of balloon-based actuators leaks, thereby adversely affecting the actuation performance of the actuator 210. Thus, the computing device 224 occasionally sends to the actuator 210 control signals for making minute adjustments to the actuation in accordance with changes to external factors such as temperature and/or pressure. It will be understood that control module 220 may thus also include sensors to monitor those external factors.

The computing device 224 may include a computer and/or other types of processor-based devices suitable for multiple applications. Such devices can include volatile and non-volatile memory elements, and peripheral devices to enable input/output functionality. Such peripheral devices include, for example, a CD-ROM drive and/or floppy drive, or a network connection, for downloading software containing computer instructions to enable general operation of the processor-based device, and for downloading software implementation programs to process input motion data and generate corresponding control information to control the actuation of an actuator. Additionally or alternatively, the computing device 224 may include a digital signal processor (DSP) to perform the various processing functions described above. A suitable DSP is the Analog Devices ADSP 2183 processor.

The computing device 224 is placed on the person's head proximate the sensing system 222, thereby minimizing the distance that signals from the sensing devices have to travel to reach the computing device to be processed. However, the location of the computing device 224 is not critical. The device 224 can thus be placed anywhere on the person's body, or even at a location not on the person's body.

FIG. 2 further shows that the vestibular stimulator also includes a power source 230 to power both the sensing system 220 and/or the actuator 210. The power source 230 may be a battery carried or attached to the person. The power source 230 is electrically coupled to the sensing system 220 and/or the actuator 210 using electrical conducting wires. Since the actuator 210 is generally implanted internally near the person's vestibular system, the electrical power wires pass subcutaneously en route to the actuator 210. Alternatively, powering of the control module 220 and the actuator 210 may be implemented through power telemetry, in which power is delivered to the actuator 210 and/or the sensing system 220 via wireless power transmission. In some embodiments the power source 230 may include several independent power units. For example, a battery for delivering sufficient power to the control module 220 could be connected directly to the control module 220 via electrical wires. A separate power unit, situated at a different location, could be used, for example, to deliver power to the actuator 210 using power telemetry.

Typically, stimulator 200 has to be calibrated. Calibration of stimulator 200 can include calibrating the motion sensing system 222. Particularly, the sensors of motion sensing system 222 are calibrated to establish the relationship between the output signals of the sensors (for instance, rotation sensors such as the sensor 500 shown in FIG. 5) and the actual translation and rotational motion undergone by the person wearing the stimulator 200. Once that relationship is determined and represented as a mathematical mapping or transformation in the form of, for example, a matrix, the output signals (typically electrical voltage levels) sensed at the various sensing devices of sensing system 222 are forwarded to the computing device of the control module 220. There the analog signals generated by the sensing devices are converted to digital signals using an analog-to-digital converter. Subsequently, the mathematical transformation or mapping determined during the calibration stage is applied to the digital signals to obtain a measure of the motion (rotational and/or translational) undergone by the person wearing the stimulator 200.

Calibration of the motion sensing system 222 can also include computation of mathematical transformations, represented by matrices, that convert the signals measured by the various sensing devices of the sensing system 222 so that the transformed motion signals are orthogonal to each other. The transformation can also be designed to translate the motion signals measured in one coordinate system to another coordinate system more suitable for generating the control signals provided to the actuator 210.

Additionally, calibration of stimulator 200 includes determining the filtering to best provide the person's motion information. Parameters that correlate the person's motion, as predicted by the model, with the control feedback signals that are provided to the vestibular system are determined. As previously noted, the control feedback signals are encoded and transmitted to the actuator 210, which then uses them to control its mechanical stimulation of the vestibular system. For example, if a high-pass filter is used to encode rotational information in a manner that mimics the normal dynamics of the canals and generates a control feedback signal needed to obtain rotational stability of a person's head, then the filter parameters would need to be determined. The determination of these parameters generally has to be performed concurrently with the determination of the level of actuation by the mechanical actuator 210, as described below.

Calibration of stimulator 200 also includes calibrating the mechanical actuation of the actuator 210. Calibration of the level of actuation by the actuator 210 is performed by examining the response of the person to various levels of actuation given controlled movement and rotation of the person's body and/or head. For example, with the actuator implanted in the person's vestibular system, the person may passively rotated or be asked to rotate his head towards a fixed pre-determined point in space. The level of actuation, given the control feedback signal received from the computing device 224, is then manually varied until the point at which the level and/or manner of actuation by the actuator 210 enables the person to improve stability and balance (e.g., until the actuation level at which the person no longer experiences some of the clinical symptoms of instability, like dizziness), or until a desired response is obtained. For example, one way to calibrate the actuator 210 is by monitoring the eye movements of the person in response to various levels of actuation. Since one of the functions of the central nervous system is to control the movement of the eye to enable clear vision during head motion, there is a strong correlation between stimulation of the vestibular system and movement of the eyes. Other ways to calibrate the actuator 210 may also be used. As was previously noted, at this stage of calibration, the filtering used to generate control signals is also determined. The filtering parameters are such that the output of the filters cause actuation of the actuator 210 in a way that enables the central nervous system to achieve improved head and/or body stability and balance.

In operation, sensing devices, such as the translation sensing device 400 and/or the rotation sensing device 500, mounted on the head of a person, sense rotational and translational motion of the head and/or body of the person. The sensing devices produce electrical signals that are sent to the computing device 224 of the control module 220. The computing device 224 processes the received signals to provide values or signals indicative of the motion undergone by the person. The processed signals are then used to produce control signals that are provided to the actuator 210. The control signals can be continuously fed signals, in which case the actuation is modified or varied on an on-going basis at short intervals. Alternatively, the control signals are sent intermittently at pre-determined intervals, in which case the actuator 210 is actuated in a consistent pattern having an amplitude, frequency and/or duration, until the next set of control signals are received by actuator 210.

Although FIG. 2 shows the stimulator 200 being used with a human being, it will be understood that the stimulator 200 can also be used with animals. It will also be understood that the stimulator 200 need not be used only to alleviate medical conditions affecting a person's balance and stability, but can be used to remedy other medical conditions where stimulation of the vestibular system is required or desirable. Further, the stimulator 200 may be used for non-therapeutic or even non-medical purposes. For example, the stimulator 200 can be used in the course of medical research to investigate the functioning of the brain.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus to stimulate the vestibular system of an individual, the apparatus comprising:
    an actuator configured
        to be in contact with a portion of the endosteum that forms the inner lining of a bony labyrinth, and
        to displace the portion of endosteum, thereby causing a displacement of a semicircular canal formed from the membranous labyrinth and suspended within perilymph that fills the bony labyrinth,
    wherein movement of the endolymph causes hairs on a cupula to bend in response to an extent of the displacement; and
    a control module coupled to the actuator that controls the actuator in response to motion information associated with the individual,
    wherein the actuator comprises one or more controls for setting one or more of an adjustable frequency of the actuator, an adjustable amplitude of the actuator, and a duration of actuation of the actuator, and
    wherein the actuator is further configured to be calibrated to determine experimentally, for a particular set of motion information of the patient, the associated at least one of the frequency of actuation, the amplitude of actuation, and the duration of actuation.

2. The apparatus of claim 1, further comprising a sensing system that provides motion information to the actuator.

3. The apparatus of claim 1, wherein the control module is configured to control the actuator by generating a control signal for transmission to the actuator.

4. The apparatus of claim 3, wherein the control module is configured to generate a control signal that includes data to control at least one of an adjustable frequency, an adjustable amplitude, and an adjustable duration of actuation.

5. The apparatus of claim 1, wherein the actuator comprises a balloon attached to a catheter, the balloon having a volume that varies in response to a control signal.

6. The apparatus of claim 1, wherein the actuator comprises a piezoelectric mechanical vibrator, the vibrator being configured to be displaced in response to a control signal.

7. The apparatus of claim 1, wherein the actuator comprises a piston, the piston being configured to be displaced in response to a control signal.

8. The apparatus of claim 1, wherein the actuator comprises an elastic membrane, the elastic membrane being configured to expand in response to a control signal.

9. The apparatus of claim 1, further comprising a power source electrically coupled to the actuator to power the actuator.

10. A method for stimulating the vestibular system, the method comprising:
    inserting an actuator in contact with a portion of an endosteum that forms the inner lining of a bony labyrinth of a patient;
    detecting a signal indicative of motion of the patient; and
    causing the actuator to press directly against the portion of the endosteum with a force sufficient to displace the portion of the endosteum, thereby causing a displacement of a semicircular canal formed from the membranous labyrinth and suspended within perilymph that fills the bony labyrinth in response to the signal, thereby causing endolymph within the semicircular canal to move in response to displacement of the portion of the endosteum by the actuator, the movement of the endolymph causing hairs on a cupula to bend in response to an extent of the displacement,
    wherein causing the actuator to displace the semicircular canal comprises at least one of setting an adjustable frequency of the actuator, setting an adjustable amplitude of the actuator, and setting a duration of actuation of the actuator, and
    calibrating the actuator to determine experimentally, for a particular set of motion information of the patient, the associated at least one of the frequency of actuation, the amplitude of actuation, and the duration of actuation.

11. The method of claim 10, wherein causing the actuator to displace the semicircular canal comprises generating control signals on the basis of the patient's motion, and transmitting the control signals to the actuator.

12. The method of claim 10, wherein causing the actuator to displace the semicircular canal comprises causing a balloon to change its volume.

13. The method of claim 10, wherein causing the actuator to displace the semicircular canal comprises causing a piezoelectric mechanical vibrator to be displaced.

14. The method of claim 10, wherein causing the actuator to displace the semicircular canal comprises causing a piston to be displaced.

15. The method of claim 10, wherein causing the actuator to displace the semicircular canal comprises causing an elastic membrane to expand.

16. An apparatus for stimulating the vestibular system of a subject, the apparatus comprising:
  means for applying a force to cause displacement of a semicircular canal formed from the membranous labyrinth and suspended within perilymph that fills the bony labyrinth, the semicircular canal containing endolymph that moves in response to displacement of the semicircular canal; and
  a control module configured for controlling the mechanical actuation of the means in response to motion information associated with the subject,
  wherein the means for applying a force includes means for setting at least one of an adjustable amplitude of force application, an adjustable frequency of force application, and an adjustable duration of force application, and
  wherein the means for applying a force is further configured to be calibrated to determine experimentally, for a particular set of motion information of the patient, the associated at least one of the frequency of force application, the amplitude of force actuation, and the duration of force application.

17. The apparatus of claim 16, further comprising a power source electrically coupled to the one or more actuators.

18. A method for stimulating the vestibular system, the method comprising:
  inserting an actuator in contact with a portion of an endosteum that forms the inner lining of a bony labyrinth of a patient;
  detecting a signal indicative of motion of the patient; and
  causing the actuator to displace the portion of the endosteum, thereby causing a displacement of a semicircular canal formed from the membranous labyrinth and suspended within perilymph that fills the bony labyrinth in response to the signal, thereby causing endolymph within the semicircular canal to move in response to displacement of the portion of the endosteum by the actuator, the movement of the endolymph causing hairs on a cupula to bend in response to an extent of the displacement, wherein
  causing the actuator to displace the semicircular canal comprises at least one of setting an adjustable frequency of the actuator, setting an adjustable amplitude of the actuator, and setting a duration of actuation of the actuator; and
  calibrating the actuator to determine experimentally, for a particular set of motion information of the patient, the associated at least one of the frequency of actuation, the amplitude of actuation, and the duration of actuation.

* * * * *